(12) United States Patent
Hudson (10) Patent No.: US 10,603,248 B2
(45) Date of Patent: *Mar. 31, 2020

(54) OCCLUSION DETECTION FOR FLOW CONTROL APPARATUS

(71) Applicant: KPR U.S., LLC, Mansfield, MA (US)

(72) Inventor: Joseph Hudson, O'Fallon, MO (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/244,479

(22) Filed: Jan. 10, 2019

(65) Prior Publication Data

US 2019/0142699 A1    May 16, 2019

Related U.S. Application Data

(63) Continuation of application No. 14/882,747, filed on Oct. 14, 2015, now Pat. No. 10,219,985.

(Continued)

(51) Int. Cl.
*A61J 15/00* (2006.01)
*F04B 43/12* (2006.01)
(Continued)

(52) U.S. Cl.
CPC ....... *A61J 15/0076* (2015.05); *A61J 15/0088* (2015.05); *A61M 5/14232* (2013.01);
(Continued)

(58) Field of Classification Search
CPC .... A61J 15/00; A61J 15/0076; A61J 15/0084; A61J 15/0088; A61M 5/14232;
(Continued)

(56) References Cited

U.S. PATENT DOCUMENTS

| 4,444,546 A | 4/1984 | Pazemenas |
| 5,720,721 A | 2/1998 | Dumas et al. |

(Continued)

FOREIGN PATENT DOCUMENTS

| EP | 2364737 A1 | 9/2011 |
| JP | 2007098125 A | 4/2007 |
| JP | 5781355 B2 | 9/2015 |

OTHER PUBLICATIONS

International Preliminary Report on Patentability Chapter I for Application No. PCT/US2015/055486, dated Apr. 18, 2017, 9 pages.

(Continued)

*Primary Examiner* — Todd Aguilera
(74) *Attorney, Agent, or Firm* — Arent Fox LLP (57) ABSTRACT

A flow control apparatus adapted for a feeding set includes a housing capable of receiving at least a portion of the feeding set and a pumping device for acting on the feeding set to produce fluid flow in the feeding set for delivery of fluid. The apparatus has a sensor arranged with respect to the pumping device to produce a signal indicative of a rotational position of a rotor, and a control circuit in communication with the sensor for receiving the sensor signal from the sensor indicative of the rotational position of the rotor and in communication with the pumping device to control operation thereof. The control circuit controls operation of a motor at a first output to rotate the rotor to produce fluid flow in the feeding set and at a second output effectively less than the first output.

14 Claims, 5 Drawing Sheets

Related U.S. Application Data (60) Provisional application No. 62/064,154, filed on Oct. 15, 2014.

(51) Int. Cl.
*A61M 5/168* (2006.01)
*A61M 5/142* (2006.01)

(52) U.S. Cl.
CPC ......... *A61M 5/16831* (2013.01); *F04B 43/12* (2013.01); *A61M 2005/14208* (2013.01); *A61M 2005/16863* (2013.01); *A61M 2205/3317* (2013.01); *A61M 2205/3365* (2013.01); *A61M 2205/50* (2013.01); *A61M 2205/502* (2013.01)

(58) Field of Classification Search
CPC ....... A61M 5/168–16895; A61M 2005/14208; A61M 2005/16863–16872; A61M 2205/3317; A61M 2205/3365; A61M 2205/50; A61M 2205/502; G05B 15/02; F04B 43/12–14
USPC .......................... 700/282; 604/31, 131, 500; 137/565.01–565.11; 417/1–47
See application file for complete search history.

(56) References Cited

U.S. PATENT DOCUMENTS

| | | |
|---|---|---|
| 6,264,634 B1 | 7/2001 | Yamazaki |
| 8,079,836 B2 | 12/2011 | Gao et al. |
| 9,889,256 B2 | 2/2018 | Cabiri et al. |
| 10,219,985 B2 * | 3/2019 | Hudson ............. A61M 5/16831 |
| 2002/0151838 A1 | 10/2002 | Beck et al. |
| 2007/0207041 A1 | 9/2007 | Gao et al. |
| 2008/0119822 A1 | 5/2008 | Knauper |
| 2008/0147008 A1 | 6/2008 | Lewis et al. |
| 2009/0191066 A1 | 7/2009 | Knauper et al. |
| 2012/0192951 A1 | 8/2012 | Yodfat et al. |
| 2013/0237955 A1 | 9/2013 | Neta et al. |
| 2013/0253420 A1 | 9/2013 | Favreau |
| 2014/0135731 A1 | 5/2014 | Breitweiser et al. |
| 2014/0330240 A1 | 11/2014 | Cabiri et al. |
| 2015/0159642 A1 | 6/2015 | Sasa et al. |

OTHER PUBLICATIONS

International Search Report and Written Opinion for Application No. PCT/US2015/055486, dated Feb. 4, 2016, 14 pages.

* cited by examiner

OCCLUSION DETECTION FOR FLOW CONTROL APPARATUS

CROSS-REFERENCE TO RELATED APPLICATIONS

The present application is a continuation of U.S. patent application Ser. No. 14/882,747, filed on Oct. 14, 2015, which claims the benefit of U.S. Provisional Patent Application Ser. No. 62/064,154, filed Oct. 15, 2014, each of which are incorporated herein by reference.

FIELD

The present invention generally relates to a flow control apparatus capable of detecting an occlusion in a tube set mounted on the apparatus.

BACKGROUND

Administering fluids containing medicine or nutrition on an ongoing basis in precise quantities to a patient is known. Typically, nutritional fluid is delivered to the patient by a pump set including a flexible elastomeric tubing loaded on a flow control apparatus, such as a peristaltic pump, which delivers fluid to the subject at a controlled rate of delivery. The peristaltic pump usually has a housing that includes a rotor driven by a motor through a gearbox. The rotor forces fluid through the flexible tubing of the pump set by the peristaltic action effected by reversible compression created by impingement, e.g., pinching, by one or more rollers mounted on the rotor. The pump set may have a valve mechanism for selectively permitting or preventing fluid flow communication through the pump set. A controller may operatively regulate the motor which effectively controls fluid flow.

Existing flow control apparatus are capable of monitoring rotation of the rotor using an encoder on the rotor. The rotation speed of the rotor can be used to determine a flow rate of the nutritional fluid being delivered through the apparatus.

Flow control apparatus may also be capable of monitoring and detecting fluid flow conditions that can occur within the loaded pump set during operation of the flow control apparatus. One such flow condition is an occlusion in the pump set. The presence of an occlusion prevents nutritional liquid from being delivered to the patient and can damage the pump set and flow control apparatus. A normal flow condition exists when there is no flow condition that would occlude or obstruct fluid flow in the pump set. However, when viscous nutritional fluids are used, pressure in the pump set may increase during otherwise normal flow conditions. Thus, if pressure is exclusively used to detect an occlusion, a normal flow condition can appear to be an abnormal flow condition when a viscous fluid is used with the pump set.

SUMMARY

There is disclosed a flow control apparatus adapted for a feeding set, said flow control apparatus comprising a housing capable of receiving at least a portion of the feeding set; a pumping device for contacting the feeding set when the feeding set is received by the housing so the pumping device acts on the feeding set to produce fluid flow in the feeding set for delivery of fluid in a patient direction to a patient, the pumping device comprising a rotor and a motor operatively connector to the rotor for rotating the rotor to act on the feeding set to produce fluid flow in the feeding set; a sensor arranged with respect to the pumping device to produce a signal indicative of a rotational position of the rotor; and a control circuit in communication with the sensor for receiving the sensor signal from the sensor indicative of the rotational position of the rotor and in communication with the pumping device to control operation thereof, the control circuit being configured to operate the motor to rotate the rotor to contact the feeding set to produce a pumping action of fluid in the patient direction through the feeding set, the control circuit operating the motor at a first output to rotate the rotor to produce fluid flow in the feeding set and operating the motor at a second output effectively less than the first output, the control circuit monitoring the sensor signal during operation of the motor at the second output to determine a flow condition in the feeding set. In some cases, the apparatus is free of a sensor to directly measure pressure in the feeding set.

There is further disclosed a method of operating a flow control apparatus including a pumping device for detecting occlusions in fluid flow in a pump set acted upon by the flow control apparatus, the method comprising operating a motor of the pumping device using the control circuit in a first output to rotate a rotor of the pumping device to produce fluid flow in the pump set; operating the motor using the control circuit at a second output effectively less than the first output; operating a sensor arranged with respect to the pumping device to produce a signal indicative of a rotational position of the rotor; and monitoring the sensor signal during operation of the motor at the second output to determine if an occlusion exists in the pump set. In some cases, the occlusion in the pump set is determined without using a sensor to directly measure pressure in the pump set. Operating the motor at the second output can comprise supplying pulses of power to the motor to rotate the rotor. The method, in some cases, can further comprise operating the motor of the pumping device using the control circuit to stop rotation of the rotor after operating the motor at the first output and before operating the motor at the second output. The method, in some cases, can further comprise determining the occlusion exists in the pump set if the rotor does not rotate to a predetermined position or does not rotate at least at a predetermined rate after operating the motor at the second output.

BRIEF DESCRIPTION OF THE DRAWINGS

Corresponding reference characters indicate corresponding parts throughout the drawings.

DETAILED DESCRIPTION

Figure 1:
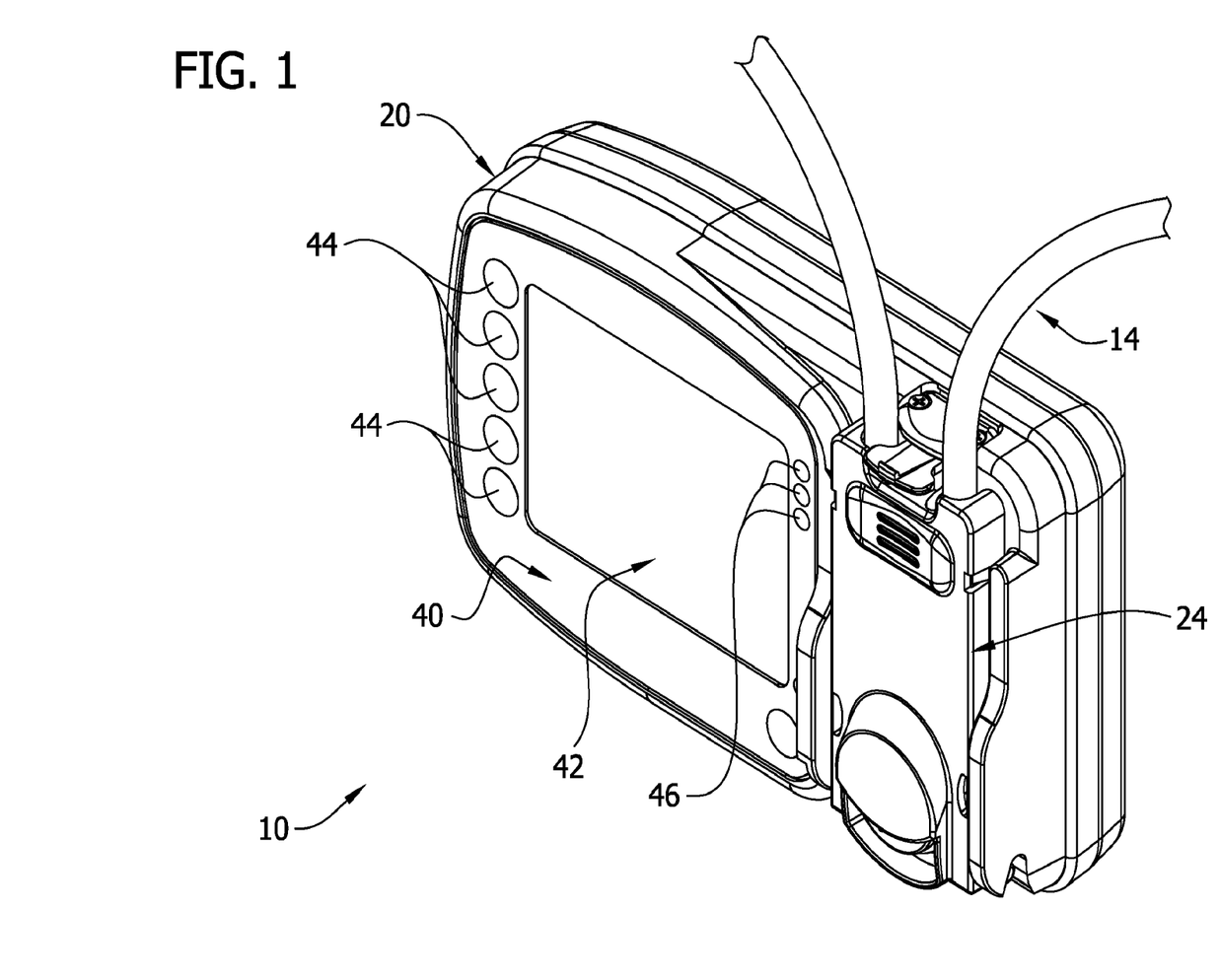
FIG. 1 is a perspective view of a flow control apparatus exemplarily shown as an enteral feeding pump and a fragmentary portion of an administration feeding set received or loaded on the pump, in accordance with one or more aspects of the invention.
Figure 2:
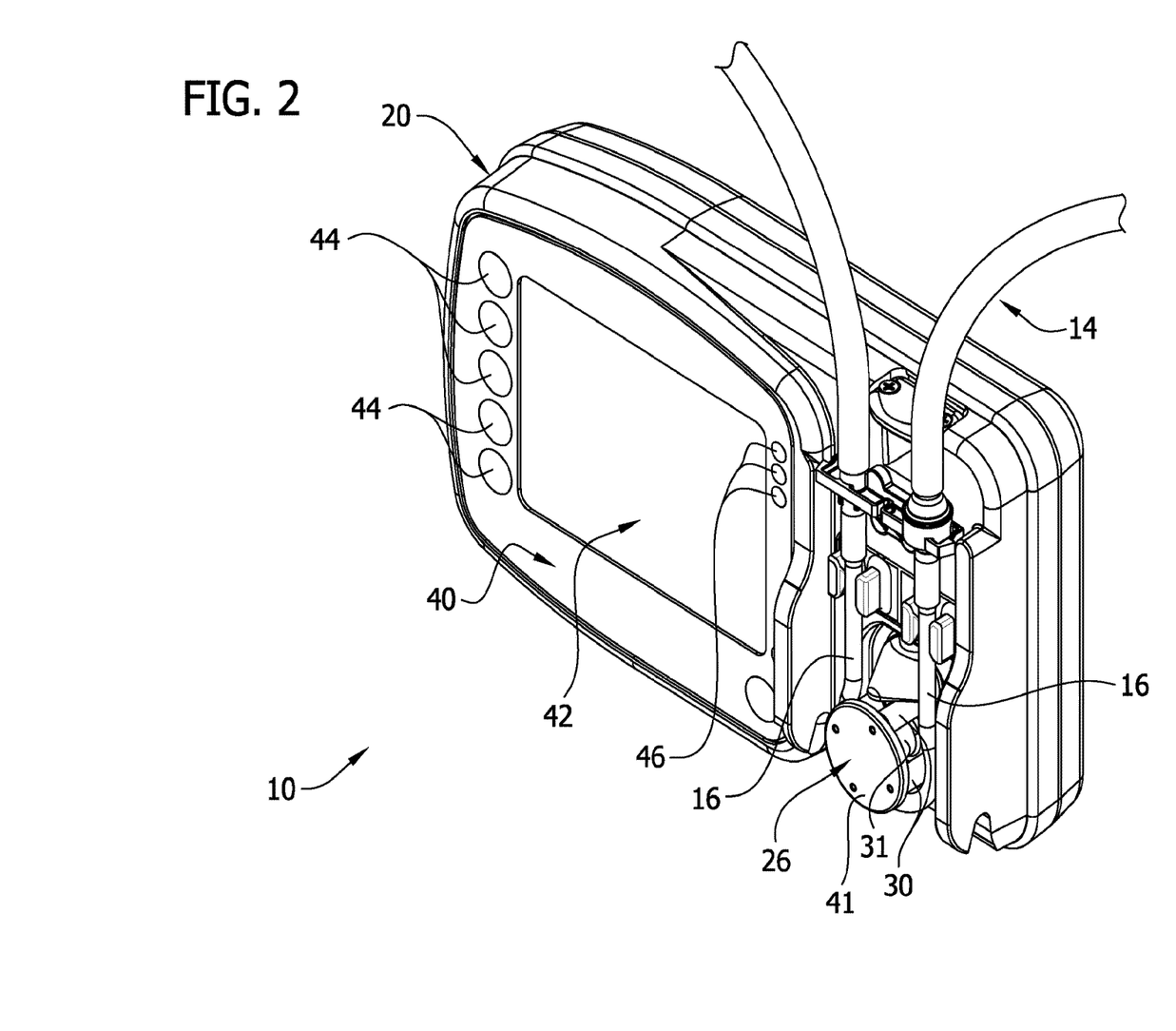
FIG. 2 is the perspective view of the flow control apparatus of FIG. 1, without a cassette housing of the feeding set.
Figure 3:
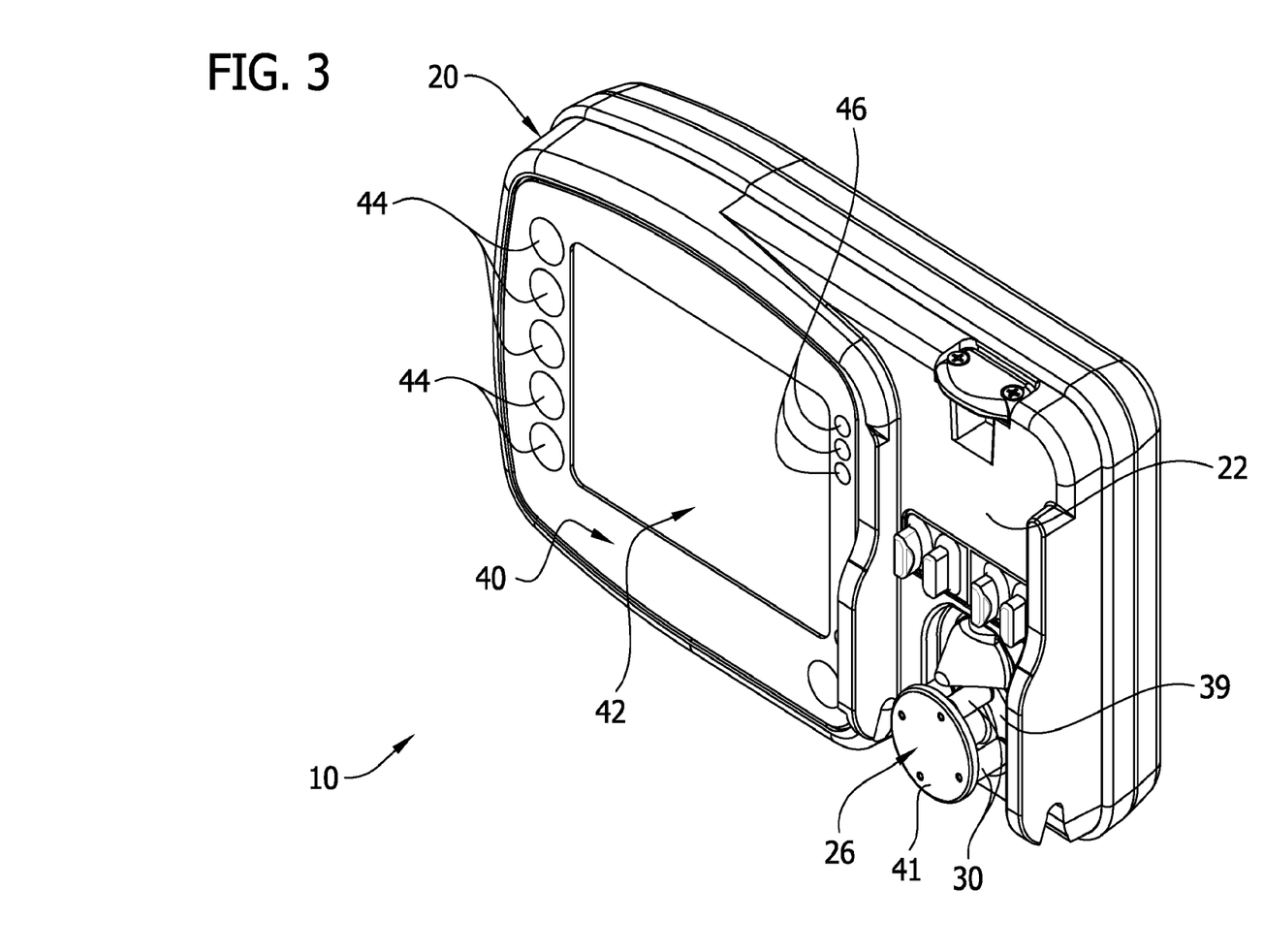
FIG. 3 is the perspective view of the flow control apparatus of FIG. 1, without the feeding set.

Referring to the drawings and in particular to FIGS. 1-3, an embodiment of a flow control apparatus is generally indicated at 10. The flow control apparatus may comprise a flow monitoring system 12 (FIG. 4) that is capable of detecting and identifying a flow condition (e.g. a downstream occlusion) present within a feeding set 14 loaded on the apparatus. The feeding set 14 may include tubing 16 that can be loaded on the flow control apparatus 10 for delivery of fluid to a patient. As used herein, the term "load" means that the tubing 16 is engaged with the flow control apparatus 10 so that the feeding set 14 is ready for operation with the flow control apparatus 10 to deliver fluid through the feeding set to a patient.

Figure 4:
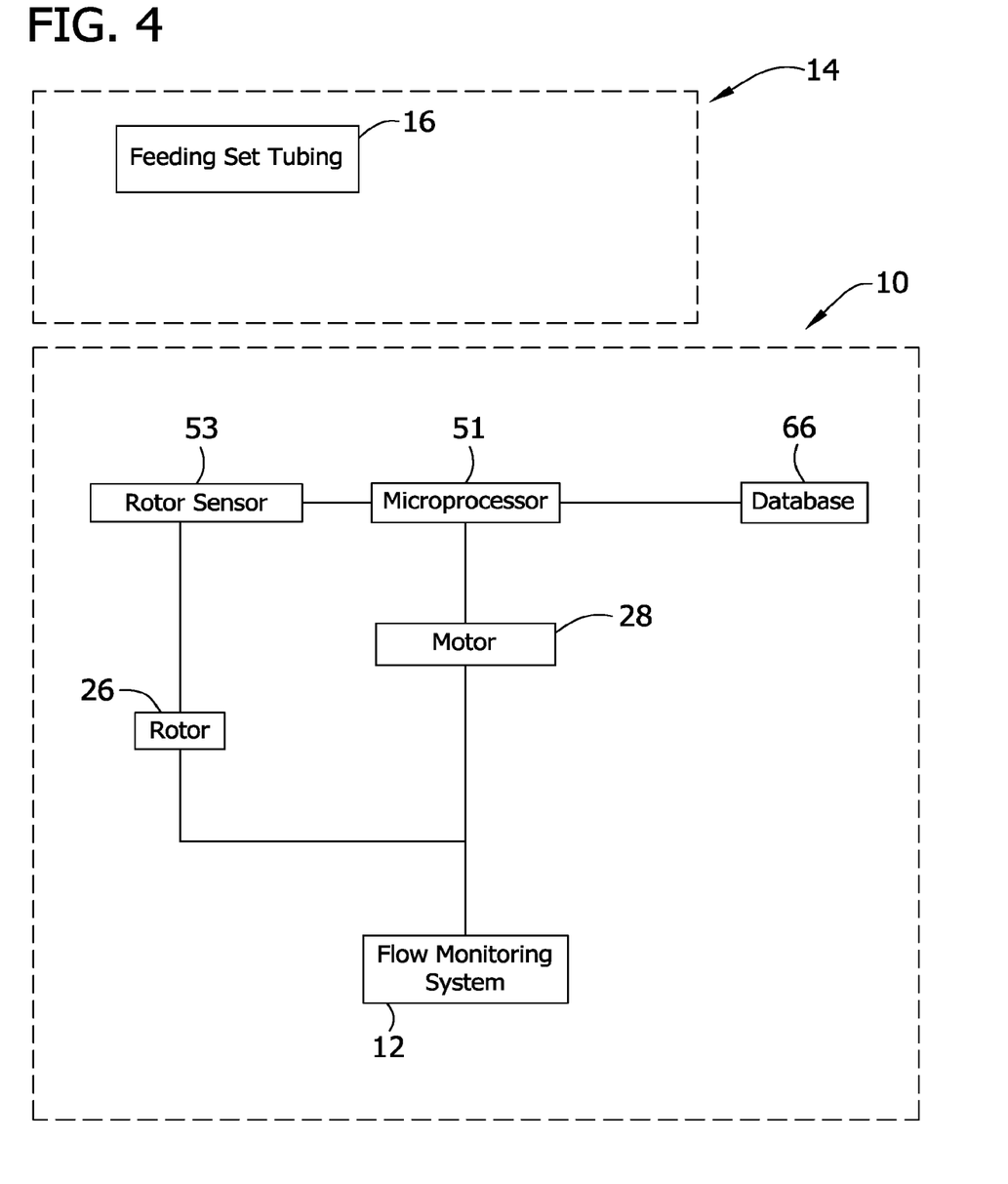
FIG. 4 is a block diagram illustrating elements of the flow control apparatus including a flow monitoring system, in accordance with one or more aspects of the invention.

The flow control apparatus 10 may comprise a housing 20 adapted for loading the feeding set 14 (broadly, "pump set") to the flow control apparatus 10. The flow control apparatus may comprise a recess 22 (FIG. 3) for receiving a cassette 24 of the feeding set 14 to load the feeding set on the flow control apparatus 10. Preferably, a means for driving fluid, such as a rotor 26, may be rotated by a motor 28 (FIG. 4). The rotor 26 includes rollers 30 (broadly, "pumping members") spaced around the rotor. The rollers 30 may be adapted to sequentially and repeatedly engage the tubing 16 so that the tubing can be compressed by the rotor (e.g., by the rollers 30) when the feeding set 14 is loaded to the flow control apparatus 10 to produce fluid flow through the feeing set by peristaltic action.

The rotor 26 may be mounted on a rotatable shaft 31 which is rotated by the motor 28. In one embodiment, the pump rotor 26 includes an inner disk 39, an outer disk 41, and preferably a plurality of the rollers 30 mounted between the inner and outer disks rotatable about their longitudinal axes relative to the disks. In the illustrated embodiment, the pump motor 28, rotatable shaft 31, and rotor 26 may broadly be considered "a pumping device". It will be understood that peristaltic pumps that use mechanisms other than rollers may fall within the scope of the present disclosure. For example, a linear peristaltic pump could be used to incorporate one or more aspects or features disclosed herein.

As used herein, the portion of tubing 16 of the feeding set 14 leading to rotor 26 is termed "upstream", while the portion of tubing 16 leading away from rotor 26 is termed "downstream". Accordingly, rotation of rotor 26 compresses the tubing 16 to drive fluid (e.g., a nutritional liquid) in a patient direction from the upstream to the downstream side of the feeding set 14. As will be explained in detail below, rotation of the rotor 26 to compress the tubing 16 can also generate positive pressure within the tubing when an occlusion is present in the tubing.

Referring to FIG. 1, flow control apparatus 10 may further comprise a user interface 40 for interaction with the flow control apparatus 10. The apparatus may also have a display screen generally indicated at 42 on the front of the apparatus that is capable of displaying information about the status and operation of the pump. Buttons 44 on the side of the display screen 42 can be provided for use in controlling and obtaining information from the pump 1, and three light emitting diodes 46 can provide status information for the pump. A user interface may have configurations other than described herein without departing from the scope of the present invention.

Referring to FIG. 4, the flow control apparatus 10 may further comprise a processor such as a microprocessor 51 in communication association with at least one rotor sensor 53. The flow monitoring system 12 may also be operatively associated with the microprocessor 51 to provide a means for the flow control apparatus 10 to detect and identify a flow condition present in the feeding set 14. The microprocessor 51 further may control and manage the operation of the various components of the flow control apparatus 10.

The at least one rotor sensor typically provides an indication of an angular position of the rotor, or the rotatable shaft and thus can be a rotary encoder. The rotor sensor 53 may be located at least partially in the housing 20 of the flow control apparatus 10 and positioned to detect a rotational position of the rotor 26. The rotor sensor 53 may comprise a plurality of first sensor elements (not shown) on a surface of the rotor 26 or on a surface that rotates conjointly with the rotor (e.g., on a surface of the rotatable shaft 31). A second sensor element (not shown) may be configured to direct a signal at the surface of the rotor 26, or at a surface that rotates conjointly with the rotor, so that the first sensor elements pass the signal emitted by the second sensor element. The second sensor element can detect when each first sensor element passes the emitted signal to determine the rotational position of the rotor 26.

The rotational position of the rotor 26 can also be used to determine a rotational speed of the rotor. Generally, a flow rate of nutritional fluid through the feeding set 14 is based on the time between rotor turns and is dependent on the rotor speed and encoder counts (i.e., number of times the first sensor elements are detected by the second sensor element). Thus, the number of encoder counts over a period may indicate the rotational speed of the rotor 26. Additionally, the first sensor elements may be arranged such that a predetermined number of encoder counts indicate a complete rotor turn. It is envisioned that other types of sensors can be used to monitor the rotational position of the rotor. The rotary encoder of the one or more sensors 53 can involve detection by measuring current generated by an magnetic field, by detecting a change in current as a result of changes induced by the presence of a magnetic field, or can involve electrical contacts that open or close a circuit to determine the rotational position. In other cases, sensors 53 can involve utilizing an optical system to determine the rotational position.

In the illustrated embodiment, the rotor 26 may include four rollers 30 so that each one-fourth of a rotation delivers one aliquot of fluid to the patient. As each roller 30 first engages the tubing 16, it pinches off the tubing thereby closing off an amount of fluid forward (i.e., toward the patient) from the fluid coming from the upstream portion of the tubing. The initial engagement that pinches off the tubing may be referred to as a "home position" for the roller 30. Thus, for example, for a rotor having four rollers there will be four "home positions" associated with the roller. The roller 30 continues to the right, e.g., in a counterclockwise rotation of the pumping device, pushing fluid forward of the roller toward the patient. Finally, the roller 30 releases engagement with the tubing 11 at about the same time a trailing roller engages the tubing for pinching it off for delivering the next aliquot of fluid. Thus, when the microprocessor 51 receives a command to deliver a selected fluid flow rate, it calculates the number of rotations within a given period of time that will deliver a number of aliquots producing the desired flow rate. It is to be understood that other ways of changing rotor operation could be used to maintain a selected flow rate. The selected flow rate may be a rate that is selected by the doctor, nurse or other caregiver, or may be a default or predetermined feeding rate programmed into the flow control apparatus 10, which can be dependent on several factors including, for example, any one or more of the patient needs and the fluid to be delivered.

The flow control apparatus 10 may also adjust a current (or voltage) applied to the motor 28 for rotating the rotor 26.

Under normal operating conditions, a baseline current may be applied to the motor 28 to rotate the rotor 26 to compress the tubing 16 with the rollers 30 and move the nutritional fluid through the feeding set 14. Typically, the baseline current level is sufficient to move both a viscous and non-viscous nutritional fluid through the feeding set 14 in a normal non-occluded flow condition and in an abnormal occluded flow condition. However, an occlusion in the feeding set 14 may drag the rotor 26 increasing resistance to the movement of the rollers 30 along the tube 16. The motor 28 may produce additional motive force or torque to overcome the increased resistance and drive the rollers 30 forward. As the motor 28 rotates the rotor 26 against the backpressure caused by the occlusion, the pressure in the feeding set would typically increase. The flow control apparatus 10 may use this increased or high-pressure condition to determine that an occlusion likely exists in the feeding set 14. For the purpose of illustration, a non-viscous fluid is considered to have a viscosity of less than about 75 cP, and a viscous fluid is considered to have a viscosity greater than or equal to about 75 cP.

The monitoring system 12 may determine through a series of decision points and steps whether normal flow or abnormal flow conditions (i.e., an occlusion) exist within the tubing 16. The monitoring system 12 varies a power (i.e., current) applied to the motor 28 while also monitoring a position of the rotor 26 to determine if an occlusion exists in the tubing 16.

Figure 5:
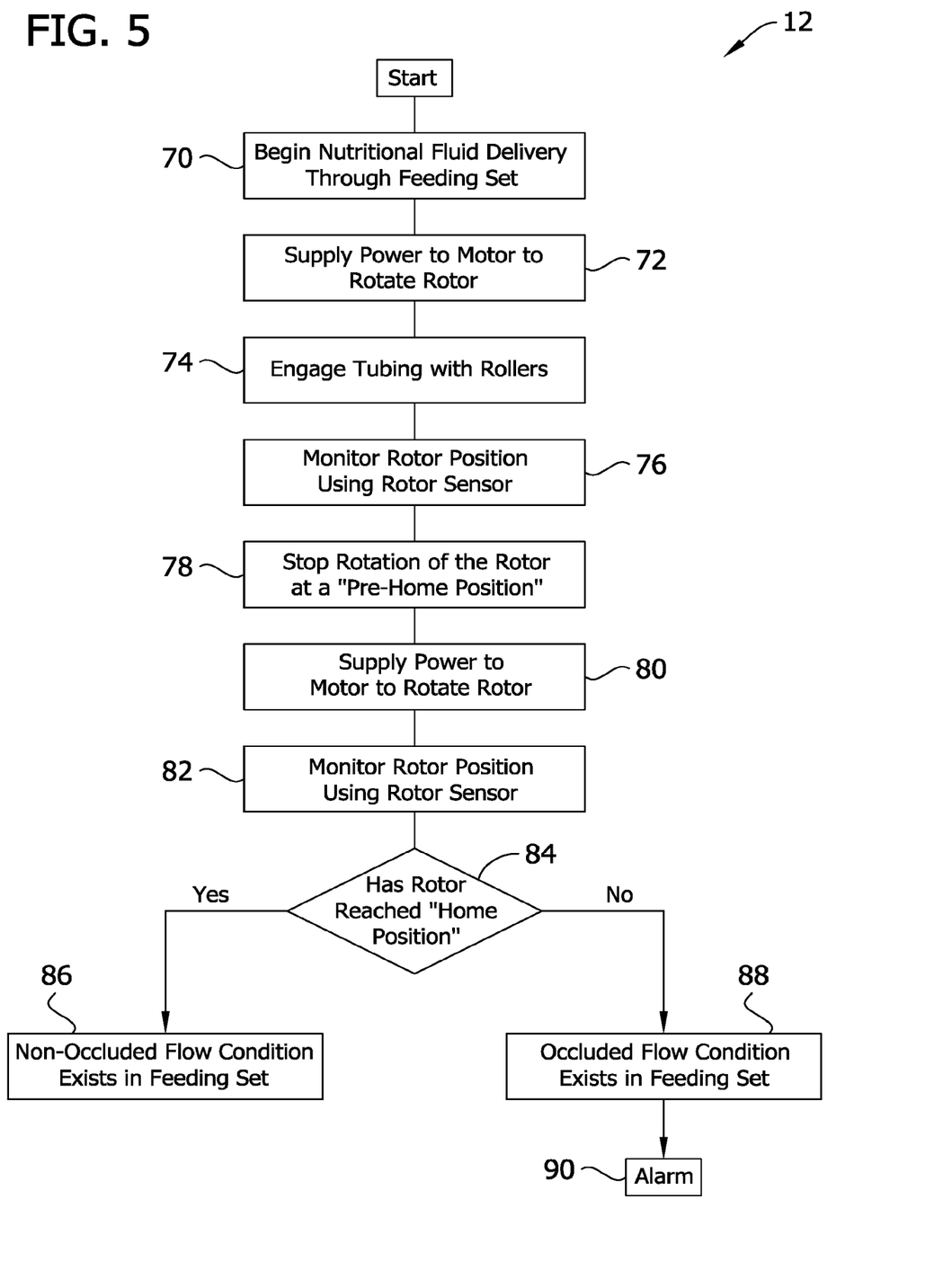
FIG. 5 is a flow chart of the flow monitoring system, in accordance with one or more aspects of the invention.

Referring to FIG. 5, the microprocessor 51 executes computer executable instructions for operating the flow control apparatus 10. At step 70, the microprocessor 31 may instruct the rotor 26 to begin rotating to deliver fluid through the feeding set 14. To rotate the rotor, at step 72, the microprocessor 51 may cause power to be supplied to the motor 28 to generate motive force. At step 74, the motive force is received by the rotor 26 having the rollers 30 engaging the tubing 16 such that the rollers engage the tubing in a peristaltic manner. Power (a "first output") may be supplied to the motor 28 such that at least the baseline current is applied to the motor to rotate the rotor 26 under both non-occluded and occluded flow conditions. As the rotor 26 rotates, at step 76, the microprocessor 51 may instruct the rotor sensor 53 to provide the microprocessor with readings of the rotor sensor signals to monitor the rotor's rotational position. The microprocessor 51 may record the sensor readings in a database 66 (FIG. 4) (broadly, "memory").

In one embodiment, the apparatus 10 can deliver fluid through the feeding set 14 to substantially complete an entire feeding cycle. For example, the microprocessor 51 may instruct the rotor 26 to rotate to deliver fluid through the feeding set 14 until only a single aliquot of fluid is left to be produced by the rotor. In the illustrated embodiment, this would be when only a quarter turn of the rotor 26 is left to complete the feeding cycle.

It will be understood that for rotors having a different number of rollers, the "pre-home position" may be disposed at a different location.

At step 78, the microprocessor 51 may instruct the rotor 26 to stop rotation at a "pre-home position" just short of the "home position". The "pre-home position" refers to a position of a roller 30 prior to engaging the tubing 16 to pinch off the tubing (i.e., prior to reaching the "home position"). In one embodiment, the "pre-home position" corresponds to a roller position where the preceding roller in the direction of rotation is in the "home position". The microprocessor 51 may use the encoder counts to determine the position of the rotor 26 to accurately stop the rotor at the "pre-home position". At step 80, microprocessor 51 may cause power to be supplied to the motor 28 to again generate motive force. The power (a "second output") applied to the motor 28 at 80 may be pulsed in short increments. Additionally or alternatively, a reduced power (the second output) from the power (the first output) supplied to begin operation of the apparatus 10 at 70 may be supplied to the motor 28. The pulsed/reduced power may be capable of adequately rotating the rotor 26 if the feeding set 14 has a non-occluded flow condition but incapable of adequately rotating the rotor if the feeding set has an occluded flow condition. At step 82, the microprocessor 51 may instruct the rotor sensor 53 to provide the microprocessor with readings of the rotor sensor signals to monitor the rotor's rotational position.

At step 84, if the rotor sensor 53 indicates that the rotor 26 reached the "home position" under the pulsed and/or reduced power within a predetermined number or pulses or within a predetermined amount of time, e.g., less than about 500 milliseconds, or, in some cases, if the fluid is less viscous, less than about 200 milliseconds, the microprocessor 51 may indicate at 86 that a normal, non-occluded flow condition exists in the tubing 16. However, if the rotor sensor 53 indicates that the rotor did not reach the "home position" under the pulsed and/or reduced power within the predetermined number of pulses or within the predetermined amount of time, the microprocessor 51 may indicate at 88 that an abnormal or occluded flow condition exists in the tubing 16.

The motor 28 failing to rotate the rotor 26 to the "home position" is a result of the lower torque condition, e.g., capability of the motor 28 being unable to overcome the back pressure generated during rotation of the rotor 26 under full power when the tubing 16 is occluded. In this condition, the motor 28 may not advance the rotor 26 at the expected speed, or may not rotate the rotor at all, and the rotor will not reach the home position in the allotted number of pulses or allotted period. The flow control apparatus 10 is thus capable of detecting an occlusion in the feeding set 14 without the use of a sensor for directly measuring pressure in the tubing 16.

It is to be understood that in the described embodiment, the flow monitoring system 12, the microprocessor 51, and database 66 may be broadly considered "a control circuit". These components may also be individually considered "a control circuit". Moreover, other types of control circuits may be used within the scope of the present invention.

The microprocessor 51 perform or initiate at least one of trigger an alarm 90 and stop operation of the flow control apparatus 10 to allow repair or replacement the feeding set 14 if an abnormal flow condition is determined. Preferably, alarm 90 may be audible, visual, tactile (e.g. vibratory) or any combination thereof. In one embodiment, the alarm 90 may cause a particular or predefined message to appear on the display 42.

The process described above where the effects of a varied motor current on the rotor position is monitored, rather than measuring a direct pressure in the tubing 16, allows the apparatus to accurately detect a flow condition in the tubing regardless of the viscosity of the fluid in the feeding set 14. By varying the output from the motor and monitoring the rotor position when the motor operates at the effectively reduced motor output, the apparatus 10 can accurately determine the flow condition in the feeding set 14 without regard for the viscosity of the fluid being used. This improves upon a system, which relies exclusively on a sensor that directly measures pressure change in the feeding set. For these reasons, the apparatus 10 and process described above provide an improved device and method for detecting flow conditions of a feeding set mounted on the apparatus.

In another embodiment, the monitoring system 12 may provide an occlusion indication or detect an additional amount of torque during an occlusion condition by reducing the power (e.g., current) to the motor during a portion of a full rotor rotation or cycle. For example, after providing nominal power to the motor for at least a portion of a full rotation, the microprocessor provides power to the motor during the remainder of the portion of the full rotation, e.g., during the last quarter of the rotor rotation or last 90 degrees of angular rotation, or during the next rotation, in predetermined time intervals, such as for a first period, e.g., an energized period of 100 milliseconds. Thereafter, the microprocessor provides no power for a second period, e.g., a de-energized period of 100 milliseconds. The amount of power delivered during the first period can be less than the nominal power. The energized and de-energized sequence can be repeated one or more times during the last quarter of the rotor rotation, or during a portion of the next rotation. Alternatively, rather than the current delivered, the voltage potential applied to the motor can be reduced from a nominal voltage during the energized and de-energized sequence. If an occlusion condition is not present, the motor will provide sufficient power to rotate the rotor to an expected position detectable by the rotor sensor, e.g., home position. If an occlusion condition is present in the tubing 16, backpressure will create resistance against rotor rotation, which will inhibit rotation of the rotor to the expected position. Confirmation of the occlusion detection can be performed by repeating the sequence and verifying the presence of the resistance to rotor movement. Upon confirmation, a notification of an occlusion condition can be displayed and the alarm can be activated. In some cases, the flow control apparatus can also be inactivated.

The amount of reduced power, e.g., lower current or lower voltage potential, may be determined based on several factors including, but not limited to, any one or more of the viscosity of the fluid to be delivered, the type of fluid delivered, the size of the tubing, the material of the tubing, the size of the rotor, the number of rollers, and the design current draw of the motor. For example, for a non-viscous fluid, the reduced power can be at less than 80% of the nominal or baseline power but for a viscous fluid, the reduced power can be at about at least 80% of the nominal or baseline power. Other non-limiting examples may involve reduced power that is less than 50% of the nominal power.

In further embodiments, the monitoring system 12 may provide an indication of an occlusion condition or detect an additional amount of torque representative of an occlusion condition by pulsing the power to the motor.

During normal operation, the flow control apparatus operates with a plurality of predefined operating periods, e.g., in one-minute periods, to provide the fluid to the patient when performing a feeding procedure. During each of the predefined operating periods, the rotor rotates at a predefined rotation rate to achieve a desired fluid feeding rate to result in a target amount of fluid delivered for the feeding procedure. Further, during each of the predefined operating periods, rotation of the rotor can be interrupted by a predefined fraction of a revolution, e.g., by one quarter of a revolution, and the monitoring system may provide pulsed power to the motor. For example, during a majority of the last full rotor rotation during the predefined operating period wherein nominal power is provided to the motor, e.g., about 400 milliamps at about 5.3 volts, the microprocessor provides pulsed power to the motor during the remainder of the portion of the last full rotation, e.g., during the last quarter of the rotor rotation or last 90 degrees of angular rotation, or during the next rotation. The pulsed power can include, for example, a first power followed by a second power. During the first power, the microprocessor can provide current and potential to the motor for a predetermined first period, e.g., an energized period. Thereafter during the second power, for example, the microprocessor provides no power for a second period, e.g., a de-energized period. In an embodiment, the magnitude of the current and potential to the motor during the energized period can be at about the nominal current and nominal potential. The duration of the energized period is typically predetermined but may be varied in view of any one or more of the following considerations; the viscosity of the fluid to be delivered, whether the fluid to be delivered is a homogeneous or heterogeneous fluid, e.g., a slurry, the physical dimensions of the tubing, and the mechanical properties of the tubing. Any of lower viscosity fluid, lower hardness material of the tubing, and smaller tubing sizes, and increased number of rollers on the rotor would involve shorter energized periods. Likewise, a higher viscosity fluid would involve longer energized period. For example, the energized period can have a duration in a range of from about 2 milliseconds to about 100 milliseconds. In an example, an enteral feeding pump can have an energized period in a range of from about 5 milliseconds to about 20 milliseconds; and a specific embodiment involves an energized period of about 10 milliseconds. The de-energized period can have a duration in a range of from about 50 milliseconds to about 500 milliseconds. In an example, an enteral feeding pump can have a de-energized period in a range of from about 100 milliseconds to about 400 milliseconds; and a specific embodiment involves an energized period of about 300 milliseconds. The duration of the de-energized period is selected to allow the rotor to rotate and approach a torque equilibrium from forces associated with the wall of the tubing and internal pressure exerted by the fluid contained therein. The durations can also be empirically determined using an expected or standard fluid such as water. Pulsing the power directed to the motor involving the energized and de-energized periods can be repeated during the last quarter of the rotor revolution, or during a portion of the next one. For example, pulsing can be repeated five times. In some configurations, pulsing including the energized and de-energized periods can be performed ten times. An exemplary configuration can involve pulsing eight times to ten times during the portion of the last full revolution during any, but preferably each, of the predefined operating period. The selection of the number of pulses typically depends on similar factors that would be considered in determining the respective duration of the energized periods and the de-energized periods. In an empirically determined example, the number of pulsed power cycles involves eight to ten cycles. Following the power pulsing a predetermined number of times, the monitoring system queries the sensor to determine if the rotor is at an expected rotational position. For example, in one configuration, the monitoring system can compare the signal from the sensor to determine if the rotor rotational position that corresponds with a roller being at a home position. If an occlusion condition is not present, the plurality of pulses will provide sufficient power to rotate the rotor to the expected position. If an occlusion condition is present in the tubing, backpressure will create resistance against rotor rotation, which will inhibit rotation of the rotor from being at the expected position. Upon determination of an occlusion condition, a notification of the occlusion condition can be displayed and, optionally, the audible alarm can be activated. In some cases, the flow control apparatus can also be de-activated with or without an audible or visible indication to attend to the occlusion condition. In still further embodiments, determination of the occlusion condition can involve delaying performing the comparison for a predetermined delay period after completion of the plurality of power pulsing events to accommodate relaxation of the tubing, if any. For example, determination can involve a delay period in a range of from about one second to about twenty seconds before comparing the sensor signal representative of the rotor's rotational position to an expected rotational position, e.g., whether a roller is at a home position. In other cases, the delay period can be commenced coincident with the first pulsing and continue or occur through the plurality the pulses and for a further time period thereafter to allow the roller to attain a position equilibrium. Thus, the duration of the delay before performing the comparison can be in a range of from about five seconds to about fifteen seconds, beginning with the first pulsing of power, or beginning after the last of the plurality of pulses.

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the microprocessor 51 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

Having described the invention in detail, it will be apparent that modifications and variations are possible without departing from the scope of the invention defined in the appended claims. For example, aspects of the invention can be directed to retrofitting or modifying a peristaltic pump that has been previously been used to include the flow monitoring system 12. Thus, some aspects of the invention can pertain to a method of modifying a previously used flow control apparatus having a pumping device, comprising installing a control circuit, in communication with a sensor for receiving a sensor signal from the sensor indicative of the rotational position of a rotor of the pumping device and in communication with the pumping device to control operation thereof, the control circuit being configured to operate a motor of the pumping device to rotate the rotor to contact a feeding set to produce a pumping action of fluid through the feeding set, the control circuit operating the motor at a first output to rotate the rotor to produce fluid flow in the feeding set and operating the motor at a second output effectively less than the first output, the control circuit monitoring the sensor signal during operation of the motor at the second output to determine a flow condition in the feeding set.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of operating a flow control apparatus including a pumping device for detecting occlusions in fluid flow in a pump set acted upon by the flow control apparatus, the method comprising:
    operating the pumping device at a first output to rotate a rotor of the pumping device to produce fluid flow in the pump set during a first portion of a feeding cycle;
    operating the pumping device at a second output less than the first output but greater than an output of zero during an entire second portion of the feeding cycle, the first portion of the feeding cycle being longer than the second portion of the feeding cycle;
    operating a sensor arranged with respect to the pumping device to produce a signal indicative of a rotational position of the rotor; and
    monitoring the sensor signal during operation of the motor at the second output to determine if an occlusion exists in the pump set,
    wherein operating the pumping device at the first output includes rotating the rotor until only a single aliquot of fluid is left to be produced by the rotor in the feeding cycle.

2. The method of claim 1, wherein the occlusion in the pump set is determined without using a sensor to measure pressure in the pump set.

3. The method of claim 1, wherein operating the motor at the second output comprises supplying pulses of power to the motor to rotate the rotor.

4. The method of claim 1, further comprising operating the motor of the pumping device using the control circuit to stop rotation of the rotor after operating the motor at the first output and before operating the motor at the second output.

5. The method of claim 1, further comprising determining the occlusion exists in the pump set if the rotor does not rotate to a predetermined position or does not rotate at least at a predetermined rate after operating the motor at the second output.

6. The method of claim 1, further comprising stopping rotation of the rotor at a pre-home position detected by the sensor prior to operating the motor at the second output.

7. The method of claim 6, wherein the rotor comprises a roller, wherein stopping rotation of the rotor comprises stopping the rotor at the pre-home position wherein the roller does not engage the feeding set.

8. The method of claim 7, wherein monitoring the sensor signal comprises monitoring whether operating the motor at the second output rotates the rotor to a home position where the roller engages the feeding set.

9. The method of claim 1, wherein operating the pumping device at the first output comprises applying at least a baseline current to rotate the rotor under both non-occluded and occluded flow conditions, and operating the pumping device at the second output comprises supplying power in pulsed increments.

10. The method of claim 1, wherein operating the motor at the second output comprises reducing power to the motor during a portion of a full rotor rotation such that the rotor rotation includes an energized period where power is supplied to the motor and a de-energized period where power is not supplied to the motor.

11. A flow control apparatus adapted to load a feeding set, said flow control apparatus comprising:
   a housing capable of receiving at least a portion of the feeding set;
   a pumping device configured to contact the feeding set when the feeding set is received by the housing so the pumping device acts on the feeding set to produce fluid flow in the feeding set for delivery of fluid in a patient direction to a patient, the pumping device including a rotor that rotates to act on the feeding set to produce fluid flow in the feeding set;
   a control circuit configured to rotate the rotor to contact the feeding set to produce a pumping action of fluid in the patient direction through the feeding set to complete a feeding cycle, the control circuit rotating the rotor to produce fluid flow in the feeding set during a first portion of the feeding cycle and rotating the rotor at a second output less than the first output but greater than an output of zero during an entire second portion of the feeding cycle, the first portion of the feeding cycle being longer than the second portion of the feeding cycle,
   wherein the control circuit rotates the rotor at the first output until a single aliquot of fluid is left to be pumped in the feeding cycle.

12. The flow control apparatus of claim 11 wherein the apparatus is free of a sensor to measure pressure in the feeding set.

13. The flow control apparatus of claim 11, wherein the control circuit operates the rotor to stop rotation of the rotor prior to operating the rotor at the second output and all within a single feeding cycle.

14. The flow control apparatus of claim 13, wherein the rotor comprises a roller, the control circuit stopping rotation of the rotor at a position wherein the roller does not engage the feeding set.

* * * * *